United States Patent
Ozaki

(10) Patent No.: US 8,267,215 B2
(45) Date of Patent: Sep. 18, 2012

(54) DRINKING LEVEL DETECTING SYSTEM AND DRINKING LEVEL DETECTING METHOD

(75) Inventor: Osamu Ozaki, Mishima (JP)

(73) Assignee: Toyota Jidosha Kabushiki Kaisha, Toyota (JP)

(*) Notice: Subject to any disclaimer, the term of this patent is extended or adjusted under 35 U.S.C. 154(b) by 346 days.

(21) Appl. No.: 12/675,876

(22) PCT Filed: Sep. 1, 2008

(86) PCT No.: PCT/JP2008/065682
§ 371 (c)(1),
(2), (4) Date: Mar. 1, 2010

(87) PCT Pub. No.: WO2009/031499
PCT Pub. Date: Mar. 12, 2009

(65) Prior Publication Data
US 2010/0212987 A1    Aug. 26, 2010

(30) Foreign Application Priority Data
Sep. 3, 2007  (JP) .................................. 2007-228127

(51) Int. Cl.
B60K 28/06  (2006.01)
(52) U.S. Cl. ........................... 180/272; 340/576; 701/45
(58) Field of Classification Search ............... 180/272; 340/576; 701/45
See application file for complete search history.

(56) References Cited

U.S. PATENT DOCUMENTS

| 4,914,038 A * | 4/1990 | Jewitt ............................ 436/132 |
| 6,697,732 B1* | 2/2004 | Gotfried ........................ 701/516 |
| 7,891,456 B2* | 2/2011 | Takahashi et al. ............ 180/272 |
| 2008/0117063 A1* | 5/2008 | Crespo .......................... 340/576 |
| 2010/0152976 A1* | 6/2010 | White et al. ................... 701/48 |

FOREIGN PATENT DOCUMENTS

| JP | A-2004-249847 | 1/2004 |
| JP | A-2005-296252 | 10/2005 |
| JP | A-2007-38872 | 2/2007 |
| JP | A-2007-106277 | 4/2007 |
| JP | U-3131821 | 4/2007 |

OTHER PUBLICATIONS

International Preliminary Report on Patentability issued in International Application No. PCT/JP2008/065682 by the International Bureau on Mar. 30, 2010.
International Search Report issued in International Application No. PCT/JP2008/065682 by the International Bureau on Sep. 30, 2008.

* cited by examiner

Primary Examiner — Ruth Ilan
(74) Attorney, Agent, or Firm — Oliff & Berridge, PLC

(57) ABSTRACT

There is provided a drinking level detecting system and a drinking level detecting method capable of improving the detection accuracy of the drinking level by allowing a third person to correct the drinking level of a driver. In a system or method which detects the drinking level of a driver of a vehicle, the drinking level of the driver is detected by an alcohol detector or the like, and the detection result is corrected by a third person other than the driver when there is an error in the detection result. Accordingly, even when the drinking level detected by the alcohol detector or the like is incorrect, the drinking level can be corrected after ensuring reliability by the determination by the third person.

8 Claims, 6 Drawing Sheets

DRINKING LEVEL DETECTING SYSTEM AND DRINKING LEVEL DETECTING METHOD

TECHNICAL FIELD

The present invention relates to a drinking level detecting system and a drinking level detecting method for detecting the drinking level of a driver of a vehicle.

BACKGROUND ART

As a known device that detects the drinking level of a driver of a vehicle, there is a device which detects the drinking level of a driver of a vehicle through the provision of an alcohol sensor in the vehicle, as disclosed in Japanese Unexamined Patent Application Publication No. 2004-249847. This device serves to prevent drunk driving by stopping an operation of a mechanism of the vehicle when the alcohol sensor exceeds a predetermined value.

[Patent Document 1] Japanese Unexamined Patent Application Publication No. 2004-249847

DISCLOSURE OF THE INVENTION

Problems that the Invention is to Solve

In such a device, however, it is difficult to raise the accuracy of the drinking level. That is, when the detection sensitivity is raised by setting the detection threshold value at which a determination of a drunken state is made to be high, the rate of incorrect detection is increased. On the other hand, when the incorrect detection rate is reduced by setting the detection threshold value at which a determination of a drunken state is made to be low, the drinking level is undetected or overlooked. Accordingly, the appropriate drinking level cannot be detected.

Therefore, the present invention has been made in order to solve such a problem, and it is an object of the present invention to provide a drinking level detecting system and a drinking level detecting method capable of improving the detection accuracy of the drinking level by allowing a third person to correct the drinking level of a driver.

Means for Solving the Problems

That is, the drinking level detecting system according to the present invention includes: a drinking level acquisition means for acquiring a drinking level of a driver of a vehicle; a third person determination means for determining whether or not it is a third person other than the driver; and a drinking level correction means for allowing a third person determined by the third person determination means to correct the drinking level acquired by the drinking level acquisition means.

According to the present invention, since the drinking level acquired by the drinking level acquisition means can be corrected by the third person other than the driver, the drinking level can be corrected after ensuring reliability by the determination of the third person even when the drinking level acquired by the thinking level acquisition means is incorrect. As a result, the detection accuracy of the drinking level can be improved.

In addition, in the drinking level detecting system according to the present invention, it is preferable that the drinking level correction means allow a third person, who is responsible for drunk driving of the driver, to correct the drinking level.

According to the present invention, since the drinking level is corrected by the third person who is responsible for drunk driving of the driver, the reliability of the detection result of the drinking level can be improved.

In addition, in the drinking level detecting system according to the present invention, it is preferable to further include an information recording means for recording third person information for specifying the third person and information regarding corrections of the drinking level so as to correspond with each other.

According to the present invention, the reliability of the determination of the third person can be improved by recording the third person information for specifying the third person and the information regarding corrections of the drinking level so as to correspond with each other.

In addition, in the drinking level detecting system according to the present invention, it is preferable that the third person be a fellow passenger of the vehicle that the driver drives or a staff member of a restaurant visited by the driver.

In addition, the drinking level detecting method according to the present invention includes: a drinking level acquisition step of acquiring a drinking level of a driver of a vehicle; a third person determination step of determining whether or not it is a third person other than the driver; and a drinking level correction step of allowing a third person determined by the third person determination step to correct the drinking level acquired by the drinking level acquisition step.

According to the present invention, since the drinking level acquired by the drinking level acquisition step can be corrected by the third person other than the driver, the drinking level can be corrected after ensuring reliability by the determination of the third person even when the drinking level acquired by the drinking level acquisition step is incorrect. As a result, the detection accuracy of the drinking level can be improved.

In addition, in the drinking level detecting method according to the present invention, it is preferable that in the drinking level correction step, a third person who is responsible for the drunk driving of the driver be allowed to correct the drinking level.

According to the present invention, since the drinking level is corrected by the third person who is responsible for the drunk driving of the driver, the reliability of the detection result of the drinking level can be improved.

In addition, in the drinking level detecting method according to the present invention, it is preferable to further include an information recording step of recording third person information for specifying the third person and information regarding corrections of the drinking level so as to correspond with each other.

According to the present invention, the reliability of the determination of the third person can be improved by recording the third person information for specifying the third person and the information regarding corrections of the drinking level so as to correspond with each other.

According to the present invention, the reliability of the determination of the third person can be improved by recording the third person information for specifying the third person and the information regarding corrects of the drinking level so as to correspond with each other.

In addition, in the drinking level detecting method according to the present invention, it is preferable that the third person be a fellow passenger of the vehicle that the driver drives or a staff member of a restaurant visited by the driver.

ADVANTAGES OF THE INVENTION

According to the present invention, the detection accuracy of the drinking level can be improved by allowing a third person to correct the drinking level of the driver.

REFERENCE NUMERALS

Figure 1:
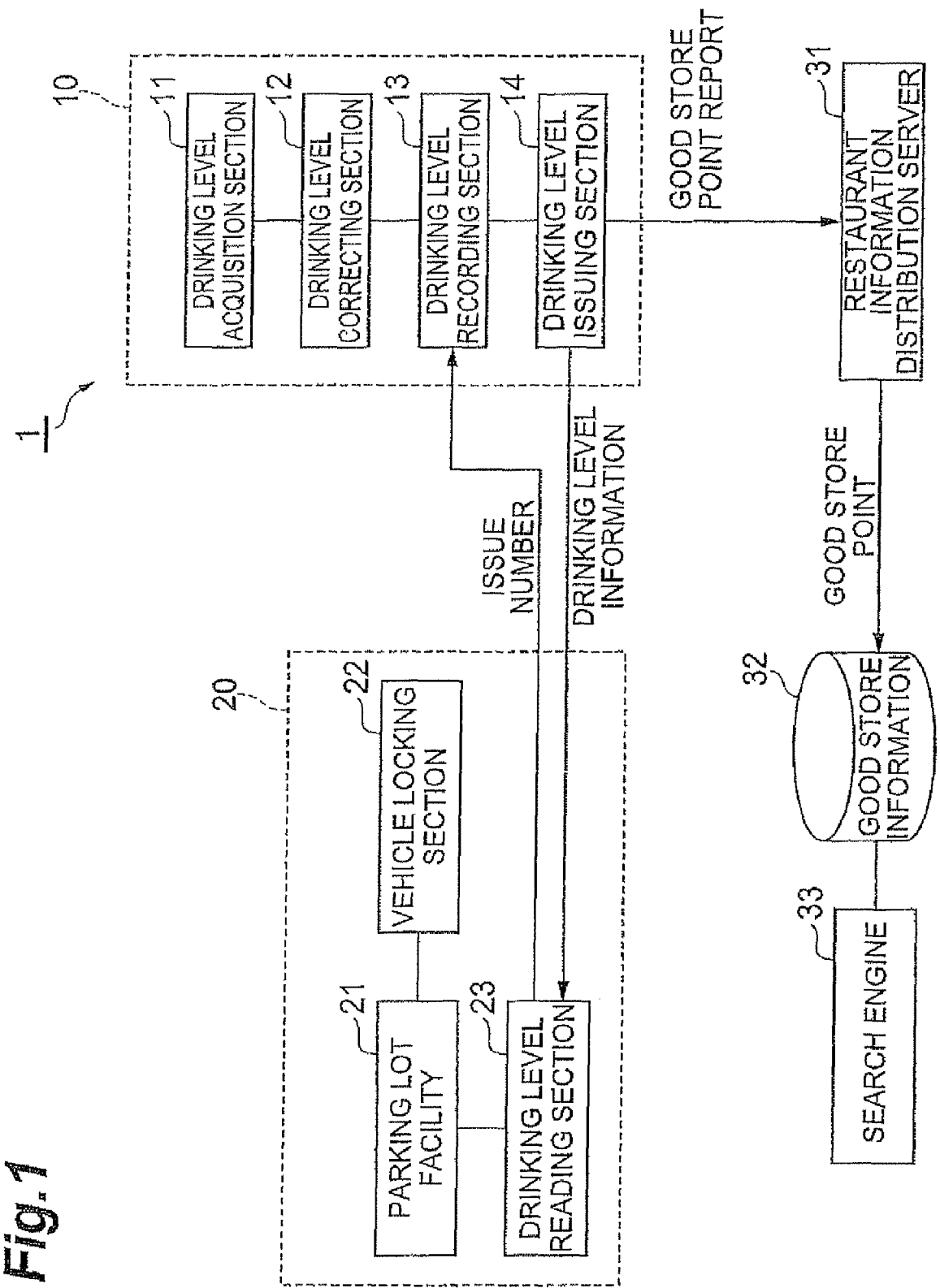
FIG. 1 is a view illustrating the schematic configuration of a drinking level detecting system and a drunk driving prevention system according to an embodiment of the present invention.

1: DRINKING LEVEL DETECTING SYSTEM
10: RESTAURANT
11: DRINKING LEVEL ACQUISITION SECTION
12: DRINKING LEVEL CORRECTING SECTION
13: DRINKING LEVEL RECORDING SECTION
14: DRINKING LEVEL ISSUING SECTION
20: PARKING LOT
22: VEHICLE LOCKING SECTION
23: DRINKING LEVEL READING SECTION

BEST MODE FOR CARRYING OUT THE INVENTION

Hereinafter, embodiments of the present invention will be described in detail with reference to the accompanying drawings. In addition, the same elements are denoted by the same reference numerals in the drawing explanations, and repeated explanation thereof is omitted.

FIG. 1 is a view illustrating the schematic configuration of a drunk driving prevention system to which a drinking level detecting system according to the present embodiment is applied.

As shown in FIG. 1, a drinking level detecting system 1 according to the present embodiment is a system that detects the drinking level of a driver of a vehicle and is provided in a restaurant 10. A drinking level acquisition section 11, a drinking level correcting section 12, a drinking level recording section 13, and a drinking level issuing section 14 are provided in the restaurant 10. The restaurant 10 is a store which serves liquor, and is a store to which the driver drives up to.

The drinking level acquisition section 11 functions as a drinking level acquisition means for acquiring the drinking level of the driver of the vehicle. For example, an alcohol detector is used. In this case, by allowing the driver who ate and drank in the restaurant to breathe his or her breath on a detection portion of the drinking level acquisition section 11, the drinking level of the driver is detected by the drinking level acquisition section 11 and it is detected whether or not it exceeds the set alcohol concentration value.

The drinking level correcting section 12 functions as a drinking level correction means for allowing a third person other than a driver to correct the drinking level detected by the drinking level acquisition section 11. For example, it is provided so that the drinking level result can be corrected by the clerk of the restaurant 10. Specifically, it is configured such that the drinking level result detected by the drinking level acquisition section 11 can be corrected by the key operation of the clerk, the operation of a button, and the like.

In this case, whether or not the operator is a clerk is checked on the basis of an ID, a password, or the like. Accordingly, the drinking level correcting section 12 also functions as a third person determination means since it has a function of determining whether or not a person who performs a correction operation is the third person other than the driver.

In addition, the correction of the drinking level referred to herein is, for example, to correct a state where the driver is determined to be drunk to a state where the driver is determined not to be drunk. In addition, the drinking level correcting section 12 may function as a means for the operation (equivalent to changing a non-drinking level to a drinking level) or release (equivalent to changing a drinking level to a non-drinking level) of an alarm, an interlock, and the like.

The clerk of a restaurant is a third person who is responsible for drunk driving of a driver of a vehicle. For this reason, corrections of the drinking level made by the clerk are very reliable. In addition, since the clerk can correct the drinking level on the basis of the state of a driver and the driver's food and drink consumption, an appropriate correction is possible. For example, when it is detected by the drinking level acquisition section 11 that the driver is drunk, the clerk can correct the drinking level of the driver to a non-drunken state if the driver is not under the influence of alcohol at all or if the driver has not drunk any liquor.

On the other hand, when it is detected by the drinking level acquisition section 11 that the driver is not drunk, the clerk can correct the drinking level of the driver to a drunken state if the driver is clearly under the influence of alcohol or if the driver has been drinking liquor within a set time.

Thus, since the drinking level of the driver can be appropriately corrected, the detection accuracy of the drinking level of the driver can be improved.

The drinking level recording section 13 records the drinking level information of the driver. For example, a personal computer having a memory is used. The drinking level information recorded in the drinking level recording section 13 is the corrected drinking level information when there was a correction by the drinking level correcting section 12 and is drinking level information acquired in the drinking level acquisition section 11 when there is no correction by the drinking level correcting section 12.

In addition, the drinking and eating level recording section 13 records an issuing number, an issuing ID, or a parking ID (hereinafter, referred to as 'issuing number and the like') of a parking ticket issued in a parking lot 20 of the restaurant 10 and records the drinking level information of the driver so as to match the issuing number and the like.

In addition, it is preferable that the drinking level recording section 13 records the third person information for specifying the third person and the drinking level information so as to correspond with each other. For example, information on the clerk who corrected the drinking level and the drinking level information are recorded so as to correspond with each other. Accordingly, since an inappropriate determination of the clerk can be prevented when determining whether or not the driver is drunk, the reliability of the determination can be improved.

The drinking level issuing section 14 issues the drinking level information of the driver recorded in the drinking level recording section 13 to the parking lot 20. As the drinking level issuing section 14, for example, a card reader/writer which records the drinking level information on a parking ticket is used. When a parking ticket is issued in the parking lot 20, the issuing number and the like are recorded on the parking ticket.

A parking lot facility 21, a vehicle locking section 22, and a drinking level reading section 23 are provided in the parking lot 20. The parking lot 20 is a parking lot of the store 10 which serves liquor. In addition, the parking lot 20 may be a parking lot for exclusive use of the store 10 and other stores. For example, when the store 10 is one store of a large commercial facility, the parking lot 20 may be a common parking lot of the large commercial facility.

The parking lot facility 21 corresponds to an apparatus which issues a parking ticket to a vehicle that has entered the parking lot 20. As long as the issuing number and the like can be recorded on the parking ticket so that the drinking level information can be recorded, any method, such as a magnetic method, may be used as a recording method. In addition, as long as it is a medium in which the parking information, the drinking level information, and the like can be recorded and from which they can be read, portable terminals such as mobile phones, vehicle keys, and the like other than the parking ticket may also be used.

The vehicle locking section 22 functions as a preventing means for preventing a vehicle, which does not satisfy the exit conditions set beforehand, exiting from the parking lot 20. For example, a wheel stopping type one which hooks the wheel of the vehicle or an outlet gate type one may be used. Cases where the exit conditions set beforehand are not satisfied could include, for example, a case where a driver of a vehicle is drunk or a case where the set parking fee is not paid.

The drinking level reading section 23 writes the issuing number on a parking ticket or reads the drinking level information recorded on the parking ticket. For example, an issuing device having card writing and reading functions is used.

The drunk driving prevention system has a good store point reporting function. When a drinking level is checked in the restaurant 10 and the drinking level information is issued, the good store point report information is transmitted to a restaurant information distribution server 31. In this case, for example, the drinking level issuing section 14 and the restaurant information distribution server 31 are connected to communicate with each other by a communication means, such as the Internet, so that the good store point report information can be transmitted and received. For example, the restaurant information distribution server 31 is provided in maintenance facilities managed by the police, cities, towns and villages, and the like.

In addition, the drunk driving prevention system has a good store information providing function. For example, the good store point information distributed from the restaurant information distribution server 31 is recorded in a good store information database 32. Search display order of the good store information recorded in the good store information database 32 is determined in consideration of the good store point information.

Accordingly, when searching restaurants through the Internet or the like by a search engine 33, the restaurants with the high good store points are preferentially displayed on the search result list. For this reason, it is possible to prevent the restaurant side from refraining from introducing the drunk driving prevention system according to the present embodiment.

Next, operations of the drinking level detecting system and drunk driving prevention system according to the present embodiment and the drinking level detecting method according to the present embodiment will be described.

Figure 2:
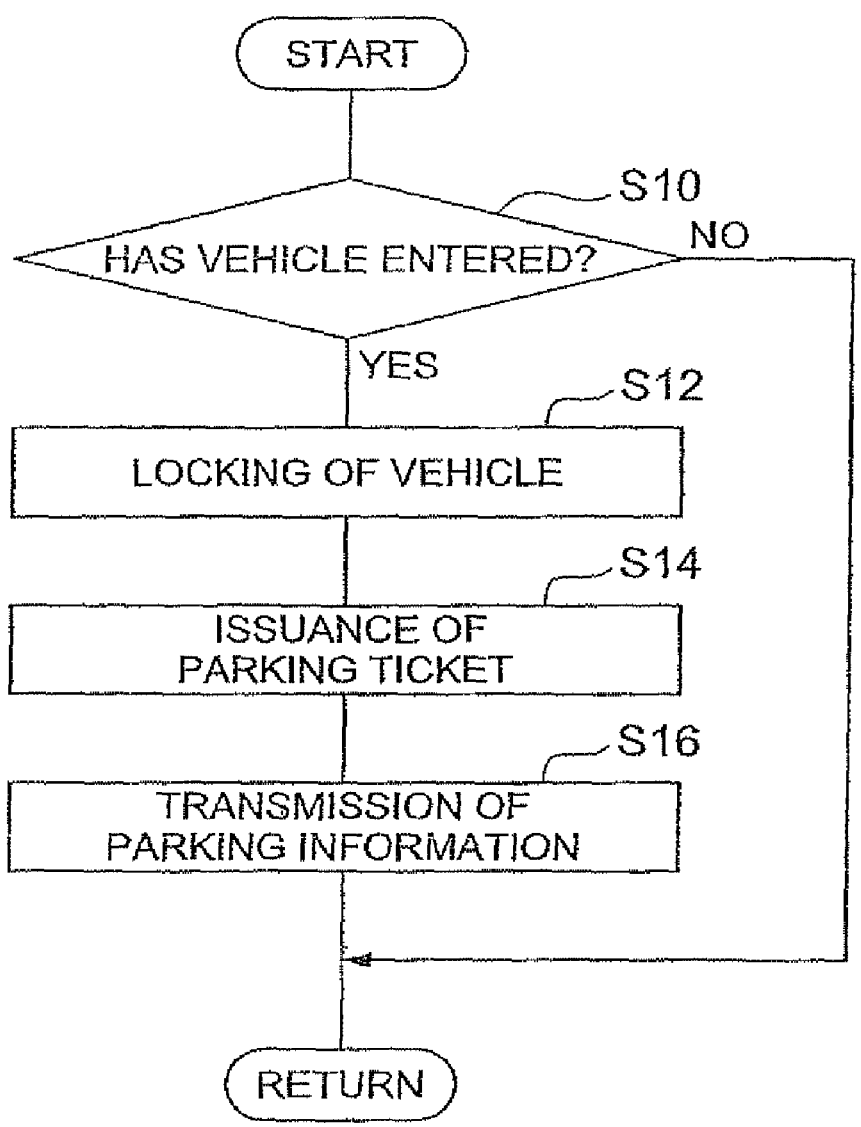
FIG. 2 is a flow chart illustrating the entrance processing of the drunk driving prevention system of FIG. 1.
Figure 3:
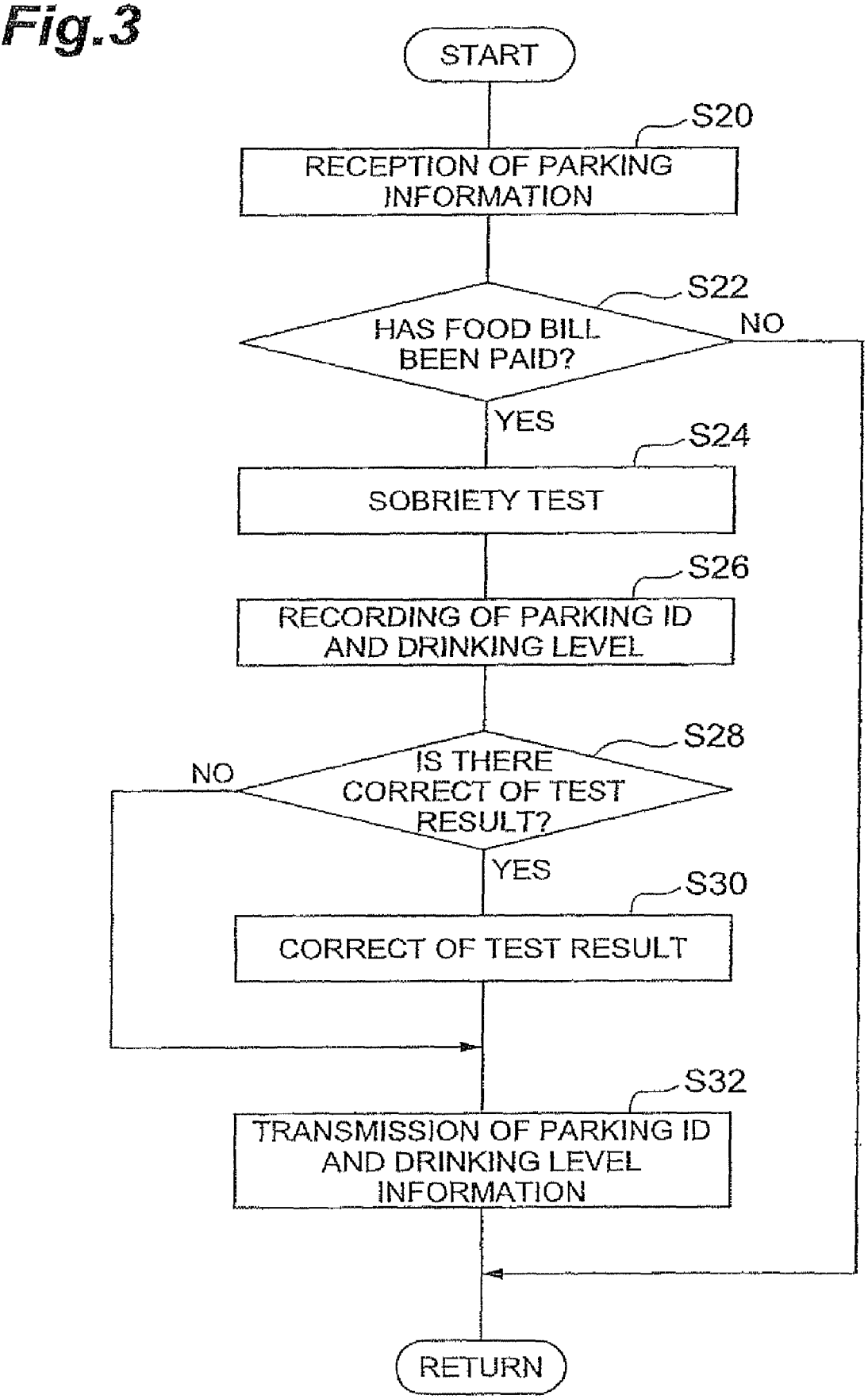
FIG. 3 is a flow chart illustrating the drinking level detection processing of the drinking level detecting system of FIG. 1.
Figure 4:
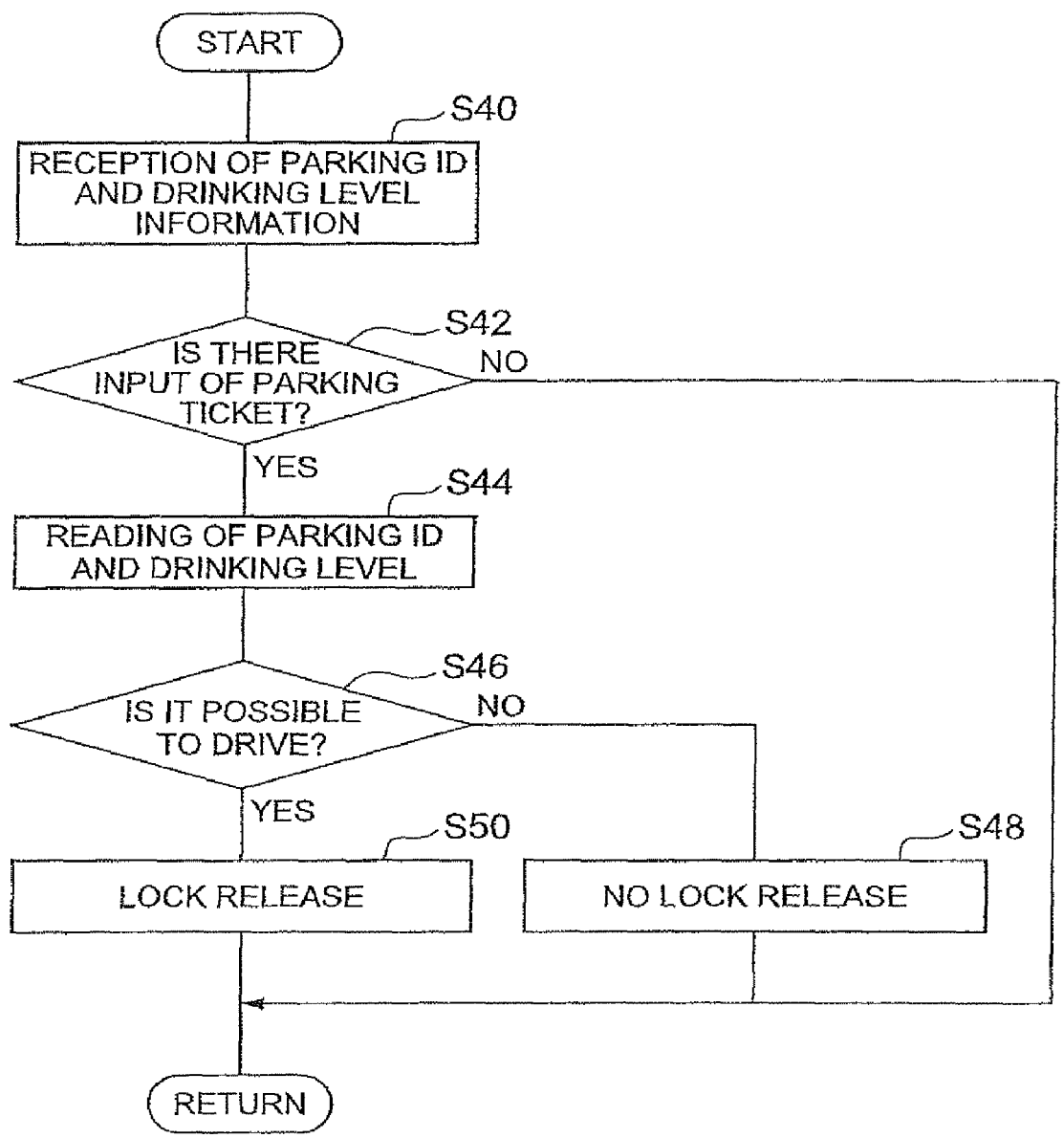
FIG. 4 is a flow chart illustrating the exit processing of the drunk driving prevention system of FIG. 1.
Figure 5:
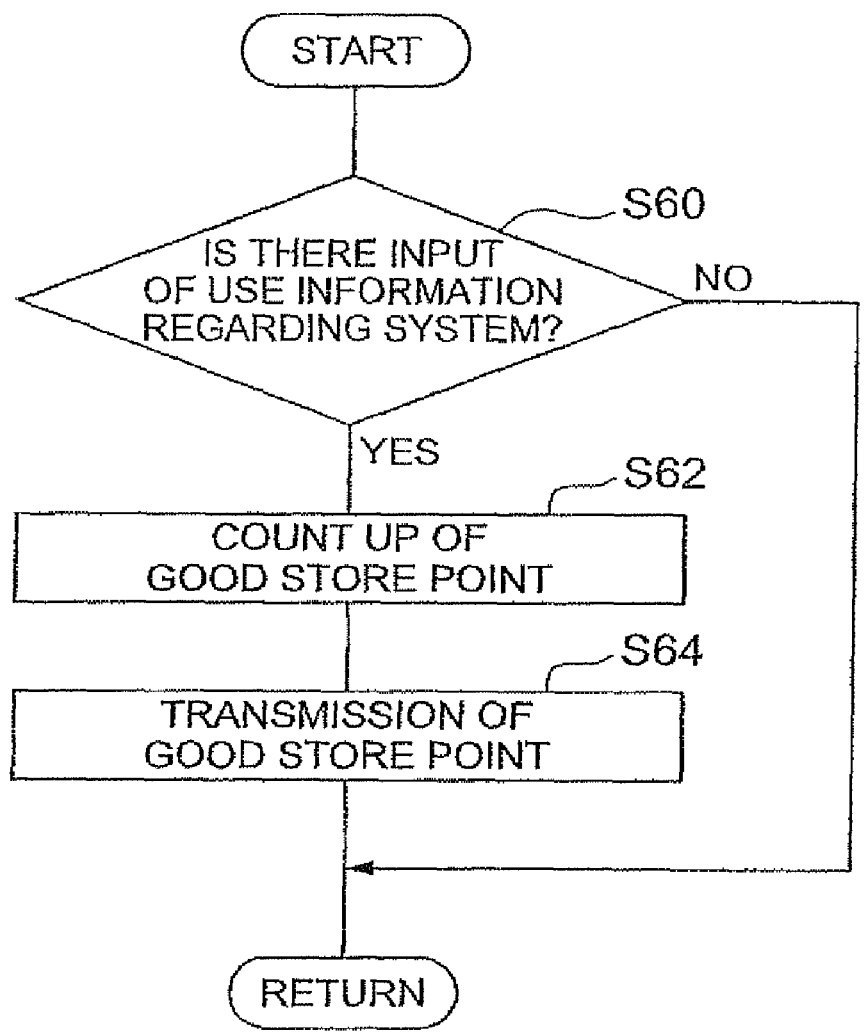
FIG. 5 is a flow chart illustrating the good store point recording processing of the drunk driving prevention system of FIG. 1.
Figure 6:
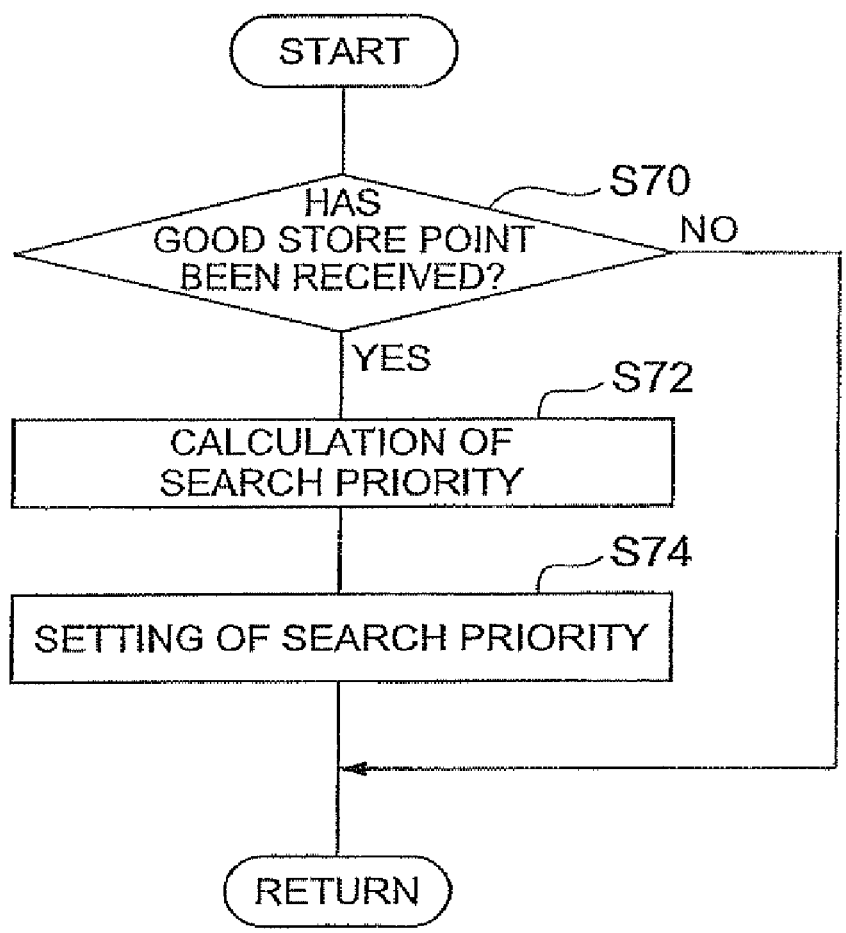
FIG. 6 is a flow chart illustrating the search priority setting processing of the drunk driving prevention system of FIG. 1.

FIG. 2 is a flow chart illustrating the entrance processing in the drunk driving prevention system, FIG. 3 is a flow chart of the drinking level detection processing in the thinking level detecting system according to the present embodiment, FIG. 4 is a flow chart illustrating the exit processing in the drunk driving prevention system, and FIG. 5 is a flow chart illustrating the good store point recording processing in the drunk driving prevention system, and FIG. 6 is a flow chart illustrating the search priority setting processing in the drunk driving prevention system.

The entrance processing in the drunk driving prevention system shown in FIG. 2 is repeatedly executed at predetermined periods by the parking lot facility 21 and the drinking level reading section 23, for example.

As shown in S10 of FIG. 2, it is determined whether or not a vehicle has entered. This determination is preferably performed on the basis of a detection signal of a sensor which detects the entrance of a vehicle. When it is determined that there is no entrance of a vehicle in S10, the entrance processing is ended. On the other hand, when it is determined that a vehicle has entered in S10, lock processing of the vehicle is performed (S12). This lock processing is processing of locking the exit of a vehicle by the vehicle locking section 22. For example, the exit of a vehicle is prevented by a wheel stopper, a gate, or the like without outputting a lock release signal to the vehicle locking section 22.

Then, the process proceeds to S14 in which parking ticket issuing processing is performed. The parking ticket issuing processing is processing of issuing a parking ticket on which the issue number and the like are recorded and is performed by the parking lot facility 21, for example. Then, the process proceeds to S16 in which parking information transmission processing is performed. The parking information transmission processing is processing of transmitting the issuing number information of the parking lot 20 to the restaurant 10. When the parking information transmission processing is finished, the control processing series of the entrance processing is ended.

By performing the entrance processing, the vehicle that has entered the parking lot 20 can be locked and the parking information corresponding to the vehicle can be transmitted to the restaurant 10.

The drinking level detection processing in the drinking level detecting system 1 shown in FIG. 3 is repeatedly executed at predetermined periods by the drinking level detecting system 1.

As shown in S20 of FIG. 3, parking information receiving processing is performed. This parking information receiving processing is processing of receiving and recording the parking information transmitted from the parking lot 20. For example, the parking information is recorded in the drinking level recording section 13.

Then, the process proceeds to S22 in which it is determined whether or not the food bill has been paid. For this determination processing, it is preferable to input an input signal of a cash register or the like to the drinking level detecting system 1 and to determine whether or not the food bill has been paid on the basis of the input signal. When it is determined that the food bill has not been paid in S22, the control processing series of the drinking level detection processing is ended. On the other hand, when it is determined that the food bill has been paid in S22, sobriety test processing is performed (S24).

The sobriety test processing is processing of testing the drinking level of the driver with a sobriety testing device, such as an alcohol detector, and of inputting the test result.

Then, the process proceeds to S26 in which the drinking level information and the parking information, such as the issuing number of the parking lot, are recorded. It is preferable that the information on whether or not the driver is drunk be recorded in the drinking level information. The parking information is preferably recorded by reading the information of the parking ticket by a card reader or the like.

Then, the process proceeds to S28 in which it is determined whether or not the drinking level information has been corrected. For example, it is determined whether or not the drinking level information has been corrected to the non-drunken state when the test result indicated the drunken state, or it is determined whether or not the drinking level information has been corrected to the drunken state when the test result indicated the non-drunken state.

It is determined by the third person other than the driver, for example, by the clerk of the restaurant whether to correct the drinking level information. In this case, it is preferable that the information regarding corrections of the drinking level information and the information on the third person who made the correction be recorded so as to correspond with each other. Accordingly, since the corrected record and the person who made the correction become clear, the reliability of the drinking level determination of the third person can be improved.

When it is determined that there was no correction in the drinking level information in S28, the process proceeds to S32. On the other hand, when it is determined that there was a correction in the drinking level information in S28, the information regarding corrections of the drinking level information is recorded (S30). Then, the process proceeds to S32 in which the drinking level information and the parking information are transmitted to the side of the parking lot 20. When the transmission processing of S32 is finished, the control processing series of the drinking level detection processing is ended.

According to the drinking level detection processing, since the drinking level detected by the alcohol detector can be corrected by the third person other than the driver, the drinking level can be corrected after ensuring reliability by the determination of the third person even when the drinking level detected by the alcohol detector is incorrect. As a result, the detection accuracy of the drinking level can be improved.

In addition, since the drinking level can be corrected by the third person who is responsible for preventing the driver from drunk driving, for example, by the clerk of the restaurant, the reliability of the detection result of the drinking level can be improved. In this case, the drinking level may also be corrected by the fellow passenger of the vehicle as a third person who is responsible for preventing the driver from drunk driving. Also in this case, since the third person who is responsible for preventing the driver from drunk driving corrects the information, the reliability of the detection result of the drinking level can be improved.

In addition, the reliability of the determination of the third person can be improved by recording the third person information for specifying the third person and the information regarding corrections of the drinking level so as to correspond with each other.

The exit processing in the drunk driving prevention system shown in FIG. 4 is repeatedly executed at predetermined periods by the drinking level reading section 23 of the parking lot 20, for example.

As shown in S40 of FIG. 4, receiving processing of the parking information, such as the issuing number, and the drinking level information is performed. This receiving processing is processing of receiving the parking information and the drinking level information transmitted from the side of the restaurant 10 and of receiving the information so as to correspond with each other.

Then, the process proceeds to S42 in which it is determined whether a parking ticket was input. For example, when the driver inserts a parking ticket in the parking lot facility 21 and the information recorded on the parking ticket is read, it is determined that a parking ticket was input. On the other hand, when the information recorded on the parking ticket is not read, it is determined that there is no input of a parking ticket.

When it is determined that there is no input of a parking ticket in S42, the control processing series of the exit processing is ended. On the other hand, when it is determined that a parking ticket was input in S42, the issue number of the parking ticket and the like are read and the drinking level information corresponding thereto is read.

Then, the process proceeds to S46 in which it is determined whether or not the driver can drive on the basis of the drinking level information. For example, when the driver is in a drunken state, it is determined that the driver cannot drive. On the other hand, when the driver is in a non-drunken state, it is determined that the driver can drive.

When it is determined that the driver can drive in S46, lock release processing is performed (S50). This lock release processing is processing of releasing the lock of the vehicle locking section 22. For example, a lock release signal is input to the vehicle locking section 22, such that the vehicle can exit. Accordingly, the driver in the non-drunken state can drive the vehicle to exit from the parking lot 20.

On the other hand, when it is determined that the driver cannot drive in S46, the lock release is not performed (S48). For example, the lock release signal is not input to the vehicle locking section 22, such that the vehicle cannot exit. Accordingly, the driver in the drunken state cannot drive the vehicle. As a result, drunk driving is prevented.

According to such exit processing, drunk driving can be reliably prevented because lock release of the vehicle of the drunk driver is not performed. In this case, since the drinking level of the driver is detected and corrected by the determination of the third person, incorrect detection or non-detection is reduced. As a result, the drinking level of the driver is accurately detected. Therefore, appropriate drunk driving prevention measures can be taken according to the drinking level.

The good point recording processing in the drunk driving prevention system shown in FIG. 5 is repeatedly executed at predetermined periods by the restaurant information distribution server 31, for example.

As shown in S60 of FIG. 5, it is determined whether or not there was input of the usage information regarding the drinking level detecting system. For example, when there was input of the good store point report information, it is determined that there was input of the usage information regarding the drinking level detecting system. On the other hand, when there is no input of the good store point report information, it is determined that there is no input of the usage infatuation regarding the drinking level detecting system.

When it is determined that there is no input of the usage information regarding the drinking level detecting system in S60, the control processing is ended. On the other hand, when it is determined that there was input of the usage information regarding the drinking level detecting system in S60, the good store points are counted up for the restaurant (S62), and the good store point of the restaurant are transmitted to the good store information database 32 (S64).

According to the good store point recording processing, when the drinking level detecting system or the drunk driving prevention system is used in a restaurant, the good store points of the restaurant are counted up and recorded. For this reason, since the restaurant receives a better evaluation with increased use of the drinking level detecting system or the drunk driving prevention system, active use of the drinking level detecting system or the drunk driving prevention system can be promoted.

The search priority setting processing in the drunk driving prevention system shown in FIG. 6 is repeatedly executed at predetermined periods by the good store information database 32, for example.

As shown in S70 of FIG. 6, it is determined whether or not the good store point information has been received (S70). When the good store point information has been received, search priority calculation is performed (S72). The search priority calculation is processing of calculating the search priority considering the good store points for a store which has received good store points. For example, the calculation is performed such that the search priority becomes high for a store which has received good store points.

Then, search priority setting processing is performed (S74). This setting processing is processing of setting the display priority of search results in consideration of the good, store point information. For example, when the conditions other than the good store point are equal, a store with high good store points is preferentially displayed as the search result.

According to the search priority setting processing, the display priority of search results when performing searching using the Internet or the like is set according to the good store points of the store. For this reason, active use of the drinking level detecting system or the drunk driving prevention system can be promoted.

As described above, according to the drinking level detecting system and drinking level detecting method according to the present embodiment, since the drinking level detected by the alcohol detector can be corrected by the third person other than the driver, the drinking level can be corrected after ensuring reliability by the determination of the third person even when the drinking level detected by the alcohol detector is incorrect. As a result, the detection accuracy of the drinking level can be improved.

In addition, since the drinking level can be corrected by the third person who is responsible for preventing the driver from drunk driving of, for example, by the clerk of the restaurant or the fellow passenger of the vehicle, the reliability of the detection result of the drinking level can be improved.

In addition, the reliability of the determination of the third person can be improved by recording the third person information for specifying the third person and the information regarding corrections of the drinking level so as to correspond with each other.

In addition, according to the drunk driving prevention system according to the present embodiment, drunk driving can be reliably prevented because lock release of the vehicle of the drunk driver is not performed. In this case, since the drinking level of the driver is detected and corrected under the determination of the third person, incorrect detection or non-detection is reduced. As a result, the drinking level of the driver is accurately detected. Therefore, appropriate drunk driving prevention measures can be taken according to the drinking level.

In addition, the above embodiments describe best embodiments of the drinking level detecting system and drinking level detecting method of the present invention, and the drinking level detecting system and the drinking level detecting method according to the present invention are not limited to those described in the present embodiment. As for the drinking level detecting system and the drinking level detecting method according to the present invention, the drinking level detecting system according to the embodiment may be modified or may be applied to other things without departing from the scope of the present invention as defined in the appended claims.

For example, although the case where the drinking level acquisition section 11 and the drinking level correcting section 12 are provided in the restaurant 10 and the vehicle locking section 22 is provided in the parking lot 20 has been described in the above embodiment, the drinking level acquisition section 11, the drinking level correcting section 12, and the vehicle locking section 22 may be provided in the vehicle. For example, it may be detected whether or not the driver is drunk by a drinking level acquisition section 11, such as an alcohol detector provided in the vehicle, and the third person determined as a third person by personal authentication or the like may correct the detection result by a switching operation or the like.

In addition, the drinking level correcting section 12 may be provided in the management center. For example, the drinking level information acquired by the drinking level acquisition section 11 is transmitted to the management center and is recorded. In addition, a configuration where the drinking level can be corrected by an operator, who is a third person, of the management center is also possible.

Industrial Applicability

According to the present invention, the detection accuracy of the drinking level can be improved by allowing a third person to correct the drinking level of the driver.

The invention claimed is:

1. A drinking level detecting system comprising:
   drinking level acquisition means for acquiring a drinking level of a driver of a vehicle;
   third person determination means for determining whether or not a person requesting correction of the drinking level is a third person other than the driver; and
   drinking level correction means for allowing the third person determined by the third person determination means to correct the drinking level acquired by the drinking level acquisition means.

2. The drinking level detecting system according to claim 1,
   wherein the drinking level correction means allows the third person, who is responsible for drunk driving of the driver, to correct the drinking level.

3. The drinking level detecting system according to claim 1, further comprising:
   an information recording means for recording third person information specifying the third person and information regarding corrections of the drinking level made by the third person in correspondence with each other.

4. The drinking level detecting system according to claim 1,
   wherein the third person is a fellow passenger of the vehicle that the driver drives or a staff member of a restaurant visited by the driver.

5. A drinking level detecting method comprising:

a drinking level acquisition step, performed by an alcohol detector, of acquiring a drinking level of a driver of a vehicle and storing the drinking level as drinking level information;

a third person determination step, performed by a drinking level correcting section, of determining whether or not a person requesting correction of the drinking level information is a third person other than the driver; and a drinking level correction step, performed by the drinking level correcting section, of allowing the third person determined by the third person determination step to correct the drinking level information stored by the drinking level acquisition step.

6. The drinking level detecting method according to claim 5, wherein in the drinking level correction step, the third person who is responsible for drunk driving of the driver is allowed to correct the drinking level information.

7. The drinking level detecting method according to claim 5, further comprising:

an information recording step of recording in memory third person information specifying the third person and information regarding corrections of the drinking level information made by the third person in correspondence with each other.

8. The drinking level detecting method according to claim 5, wherein the third person is a fellow passenger of the vehicle that the driver drives or a staff member of a restaurant visited by the driver.

* * * * *